US005741637A

United States Patent [19]

Rueger et al.

[11] Patent Number: 5,741,637
[45] Date of Patent: Apr. 21, 1998

[54] PROCESS FOR THE PRODUCTION OF MODIFIED NUCLEIC ACIDS

[75] Inventors: Rüdiger Rueger, Seeshaupt; Christoph Kessler, Dorfen, both of Germany

[73] Assignee: Boehringer Mannheim GmbH, Mannheim, Germany

[21] Appl. No.: 254,422

[22] Filed: Jun. 6, 1994

Related U.S. Application Data

[63] Continuation of Ser. No. 126,133, Sep. 24, 1993, abandoned, which is a continuation of Ser. No. 642,331, Jan. 17, 1991, abandoned.

[30] Foreign Application Priority Data

Jan. 17, 1990 [DE] Germany .......................... 40 01 154.2

[51] Int. Cl.$^6$ .............................. C12Q 1/68; C12P 19/34
[52] U.S. Cl. .............................. 435/6; 435/91.2; 935/77; 935/78
[58] Field of Search ......................... 435/6, 91.2; 935/77, 935/78

[56] References Cited

U.S. PATENT DOCUMENTS

| | | | |
|---|---|---|---|
| 4,358,535 | 11/1982 | Falkow et al. .................... | 435/6 |
| 4,581,333 | 4/1986 | Kourilsky et al. ................ | 435/6 |
| 4,683,195 | 7/1987 | Mullis et al. ..................... | 435/6 |
| 4,683,202 | 7/1987 | Mullis ............................. | 435/6 |
| 4,711,955 | 12/1987 | Ward et al. ...................... | 435/6 |
| 4,851,331 | 7/1989 | Vary et al. ....................... | 435/6 |
| 4,965,188 | 10/1990 | Mullis et al. .................... | 435/6 |

FOREIGN PATENT DOCUMENTS

| | | |
|---|---|---|
| A-0122614 | 10/1984 | European Pat. Off. . |
| A-0139489 | 5/1985 | European Pat. Off. . |
| A-0200362 | 12/1986 | European Pat. Off. . |
| A-0201184 | 12/1986 | European Pat. Off. . |
| A-0 297 379 | 1/1989 | European Pat. Off. . |
| A-0 317 074 | 5/1989 | European Pat. Off. . |
| A-0 357 011 | 3/1990 | European Pat. Off. . |
| A-0 370 694 | 5/1990 | European Pat. Off. . |
| WO 86/07387 | 12/1986 | WIPO . |
| WO 89/09281 | 10/1989 | WIPO . |
| WO 89/11546 | 11/1989 | WIPO . |
| WO 90/02205 | 3/1990 | WIPO . |

OTHER PUBLICATIONS

Gene Anal. tech. 6, 79 (1989) Jansen et al.
Nucleic Acids Research 16, 8719 (1988) Lo et al.
Anal. Biochem. 178,239 (1989) Mitchell et al.
Nucleic Acids Research 16, 11327 (1988) Syvänen et al.
Nucleic Acids Research 147, 4937 (1989) Hultman et al.
Proc. Natl. Acad. Sci. USA 86, 2423 (1989) Kemp et al.
Nature 340, 733 (1989) Uhlen.
Proc. Natl. Acad. Sci. USA 86, 2757 (1989) We et al.
Nucleic Acids Research Symp. Ser. 20, 91 (1988) Yamane et al.
Anal. Biochem. 177, 90 (1989) Schowalter et al.
Proc. Natl. Acad. Sci, 1986 6230–6234 Saiki et al.
Proc. Natl. Acad. Sci, 1990, 87, 8923–8927 D.A. Nickerson et al.
Heiles et al., Biotechniques 6(10):978–981 (1988).
Lo et al., Nuc. Acids Res. 16(17):8719 (1988).
Misiura et al., Ibid. 18(15):4345–4354 (1990).

*Primary Examiner*—Stephanie W. Zitomer
*Attorney, Agent, or Firm*—Nikaido Marmelstein Murray & Oram LLP

[57] ABSTRACT

Process for the production of nucleic acids by hybridization of at least one primer to a template nucleic acid and enzymatic elongation of the primer to a nucleic acid strand which is complementary to the template nucleic acid by reaction with different types of nucleoside triphosphates, wherein the complementary nucleic acid strand carries two or more groups which enable it to be immobilized and one or more detectable groups, a method which uses this process for the detection of nucleic acids, suitable reagent kits therefor and modified nucleic acids.

13 Claims, 1 Drawing Sheet

PROCESS FOR THE PRODUCTION OF MODIFIED NUCLEIC ACIDS

This application is a continuation of application Ser. No. 08/126,133, filed Sep. 24, 1993, now abandoned, which is a continuation of application Ser. No. 07/642,331, filed Jan. 17, 1991, now abandoned.

Process for the production of modified nucleic acids he invention provides a process for the production of modified nucleic acids, a method for the detection of nucleic acids which encompasses this production process, reagents for carrying out these processes, as well as a nucleic acid which is produced in the said processes.

Methods for the detection of nucleic acids have increasingly proven to be a sensitive alternative to immunologic tests in clinical diagnostics, for example in the area of human diagnostics such as e.g. virus diagnostics and baterial diagnostics. However, methods for the detection of nucleic acids have also been applied to food diagnostics and histology. In these methods the material containing the nucleic acid to be detected is brought into contact with a nucleic acid which is complementary to the nucleic acid to be detected. The formation of a nucleic acid hybrid can subsequently be visualized in different ways. Such a method is described for example in DE-A-2801582 or U.S. Pat. No. 4,358,535.

These methods are, however, less well suited for the detection of very small amounts of nucleic acid. In order to improve these methods it was suggested in EP-A-0200362 that the nucleic acid to be detected is multiplied in a step prior to the hybridization reaction by an in vitro system. For this purpose at least one so-called primer is added to the sample per nucleic acid single strand to be detected. Starting from the primer, a nucleic acid strand complementary to the template nucleic acid is formed for each of the nucleic acid single strands by means of an enzymatic elongation reaction via reaction with mononucleotides. This reaction can be carried out several times in succession whereby the newly formed nucleic acid strands can also be multiplied. A disadvantage of this method as well as of the above-mentioned methods according to the state of the art is that a hybridization reaction with a labelled nucleic acid is carried out following the multiplication reaction.

A blotting method is suggested in EP-A-0324474 in which hybridization with a labelled nucleic acid probe can be omitted as a result of the incorporation of a labelled mononucleotide into the newly formed nucleic acid. A disadvantage of this method is, however, that the nucleic acid has to be separated by means of gel chromatography. This involves complicated apparatus and is time-consuming.

The object of the present invention was to avoid the disadvantages of the state of the art and in particular to provide simpler and particularly sensitive methods requiring fewer steps for the detection of nucleic acids.

The invention provides a process for the production of nucleic acids by hybridization of at least one primer to a template nucleic acid and enzymatic elongation of the primer to a nucleic acid strand which is complementary to the template nucleic acid by reaction with at least four different types of mononucleotides whereby the complementary nucleic acid strand carries two or more groups which enable it to be immobilized and one or more detectable groups. The invention also provides a method for the detection of nucleic acids, a reagent for the production of nucleic acids, a reagent kit for the detection of nucleic acids and a nucleic acid produced in one of the above processes.

Within the scope of the invention template nucleic acids are in particular DNA and RNA of prokaryotic or eukaryotic origin. They also include viral and bacterial nucleic acids as well as nucleic acids from viroids. They can be single or double stranded. They can be episomal nucleic acids such as plasmids or genomic, chromosomal nucleic acids. The nucleic acids can be characteristic for a particular organism or for a group of organisms. The nucleic acids can also be nucleic acids which have already been pretreated, for example nucleic acids cleaved by means of restriction enzymes. In the case of RNA, cDNA should be produced beforehand. It has proven to be advantageous when the nucleic acids are present in a single-stranded form or are brought into a single-stranded form before carrying out the reaction.

Special nucleic acids which are present in the sample and which form the basis for the detection or production reaction are denoted template nucleic acids in the following.

The template nucleic acid can be present in a purified form or also in a mixture with other nucleic acids which are not to be detected or to be used.

These nucleic acids can be contained in a solid or liquid sample which is pretreated or non-pretreated. The template nucleic acids are preferably contained in a sample which is obtained by lysis of an organism, for example a cell, and which contains a great variety of compounds among which are also other nucleic acids.

In order to carry out the process according to the present invention for the production of nucleic acids at least one, and preferably one primer per nucleic acid single strand is added under suitable conditions to the sample which contains a template nucleic acid. This primer is preferably an oligonucleotide of 12 to 60, in particular 15 to 30 nt (nucleotides) length. The primer can hybridize with a particular region of the template nucleic acid. This is possible if the primer has a nucleotide sequence which is essentially complementary to a region of the template nucleic acid.

The primer is preferably constructed of deoxyribonucleotides or ribonucleotides whereby these nucleotides can be modified or unmodified. Most of the nucleotides of the primer are preferably unmodified.

Unmodified nucleotides are the nucleotides which occur naturally, for example adenosine, guanosine, thymidine, uridine and cytidine. Modified nucleotides are nucleotide analogues such as 7-deaza-adenosine or 7-deaza-guanosine or derivatives of the said unmodified nucleotides which contain an (immobilizable) group which enables the immobilization or a detectable group.

Groups which are capable of immobilizing are for example chemical groups which can be bound covalently to a solid phase, for example by a chemical reaction or by a photoreaction, or groups or parts of molecules which are recognized and can be bound by another molecule or part of a molecule via group-specific interactions. Such groups are therefore e.g. haptens, antigens and antibodies, glycoproteins, for example lectins, or also the binding partners of binding proteins, such as biotin or iminobiotin. Haptens and vitamins are preferred, biotin or steroids such as digoxigenin are especially preferred.

Detectable groups are for example covalently bound, directly detectable groups or parts of molecules, such as radioisotopes, fluorescent dyes or chromophoric substances, or also groups which are indirectly detectable by means of a subsequent reaction. These include in particular those biospecic groups as described above for the groups which are capable of immobilizing. Digoxigenin is particularly preferred.

The primer can contain one or several such groups which enable the immobilization or detectable groups. It can also be comprised of one or more groups which enable the immobilization as well as one or more detectable groups. The primer preferably contains none whatever of these groups.

Such primers can be produced in a manner known to the expert, for example by chemical synthesis in analogy to WO 84/03285 or by enzymatic incorporation in analogy to EP-A-0063879. The primer can be modified at any position, preferably, however, not at the 3' end. Modification at the 5' end is for example possible (for example according to Molecular Cloning, p. 239 (1982) Ed. Maniatis et al., CSH) or/and via the nucleobases for example via an ε-aminocaproic acid linker and/or via random priming according to Feinberg et al. (Anal. Biochem. 132, 6 (1983)). All primers which are described in EP-A-0200362 are also in principle suitable.

The conditions under which a hybridization of the primer with its matching part of the template nucleic acid takes place are known to the expert, for example from EP-A-0200362. They depend on the length of the primer as well as on the extent of the complementarity.

The primer should have at least one nucleotide, in particular at its 3' end, which is complementary to the corresponding nucleotide of the template nucleic acid. The primer can, in addition, contain a nucleotide sequence, preferably at the 5' end, which is not complementary to the template nucleic acid. It can also contain recognition sites for enzymes, for example polymerases; in addition proteins can also be bound.

The nucleotide sequence of the primer is chosen so that the single-stranded nucleotide sequence of the template nucleic acid extends beyond the 3' end of the primer after hybridization.

In the process according to the present invention for the production of nucleic acids the hybrid nucleic acid formed from template nucleic acid and primer is elongated at the 3' end of the primer by formation of a piece of nucleic acid joined to the primer which is complementary to the above-mentioned single-stranded region of the template nucleic acid. This can be carried out analogous to EP-A-0200362. The elongation described there is by means of four mononucleotide triphosphates.

In the process according to the present invention modified as well as non-modified nucleoside triphosphates are employed as mononucleoside triphosphates. Modified nucleoside triphosphates are the triphosphates of the above-mentioned modified nucleotides. Examples of such modified mononucleoside triphosphates are digoxigenin-dUTP (EP-A-0324474) or biotin-dUTP. In the elongation reaction those nucleoside triphosphates which carry a group which enables them to be immobilized and those nucleoside triphosphates which carry a detectable group can be employed at the same time as the modified nucleoside triphosphate. The group which enables the immobilization is preferably in this case a different group from the detectable group. If certain experimental conditions are adhered to it can be ensured that several groups which enable the immobilization are incorporated into the newly formed nucleotide sequence when the elongation is more than ca. 30–40 nucleotides. Preferably not all nucleoside triphosphates are modified. It is particularly preferred if one type of nucleoside triphosphate in modified form is employed as well as the 4 natural types of nucleoside triphosphates.

The amount of the unmodified nucleoside triphosphate which is also employed in a modified form is preferably reduced by the amount of modified nucleoside triphosphate used so that the total amount of this type of nucleoside triphosphate remains approximately the same. The amount of the different types of mononucleoside triphosphates is in each case approximately the same and is known to the expert. For example in an elongation analogous to EP-A-0200362 it is preferably 100 μM–300 μM, particularly preferably ca. 200 μM.

By means of the following embodiments of the process according to the present invention it is possible to produce nucleic acids which contain at least one detectable and two or more groups which enable them to be immobilized and which are at least partially complementary to a template nucleic acid:

Use of a primer which contains at least one detectable group and of a type of nucleoside triphosphate which contains an immobilizable group. In this case the primer can also in addition contain one or several immobilizable groups and in addition a type of nucleoside triphosphate can be used which contains a detectable group. However, the embodiments in which the primer does not have an additional detectable group are preferred.

Use of a primer which contains at least one immobilizable group and nucleoside triphosphates which contain a detectable group, as well as nucleoside triphosphates which contain an immobilizable group. Also in this case the primer can in addition also contain a detectable group.

Use of a primer which contains more than one immobilizable group and nucleoside triphosphates which contain a detectable group. In addition, nucleoside triphosphates can also be used which contain an immobilizable group.

Use of a primer which does not contain an immobilizable or a detectable group and mononucleoside triphosphates which contain a detectable group as well as mononucleoside triphosphates which contain an immobilizable group. This situation is preferred since in this case a reaction for the modification of the primer is omitted. In addition, by the incorporation of detectable as well as of immobilizable mononucleotides, it is ensured that the nucleic acid formed contains a multitude of immobilizable groups and at least one detectable group. A further advantage of this variant is the considerable facilitation of the separation of the nucleic acids formed from non-reacted primers.

Enzymes come into consideration as the enzyme for the elongation of the primer which exhibit DNA- or RNA-dependent DNA or RNA polymerase activity. Thermostable DNA polymerases are preferred. These include for example taq DNA polymerase or the Klenow fragment of the E. coli DNA polymerase.

The elongation reaction preferably ends at the 5' end of the template nucleic acid. It can, however, if desired, be interrupted prematurely by use of stop reagents e.g. stop nucleotides. If necessary the newly formed piece of nucleic acid is finally ligated to the primer, for example via the ligase reaction.

By means of the enzyme catalysed reaction and using modified and unmodified mononucleoside triphosphates, the primer is elongated by one piece of nucleic acid which is complementary to the corresponding part of the template nucleic acid. The newly formed nucleic acid then contains two or more groups which enable it to be immobilized and one or more detectable groups. It has turned out that it is very advantageous if two or more groups which enable it to be immobilized are contained in a strand of the newly formed nucleic acid. In particular such nucleic acids can be immobilized more efficiently than those which only have one such group. This facilitates a quantification of the initial amount of template nucleic acid by a more exact quantification of the newly formed nucleic acids.

The number of detectable groups in each newly formed strand is preferably more than 1 and it is especially preferable if ca. every 15th to 30th nucleotide has a detectable group.

With the process according to the present invention nucleic acids can for example be produced which have a length of 100 to 8000 bp. It is, however, practically only limited by the enzyme system which carries out the elongation.

Depending on the further application of the amplification products the newly formed nucleic acids can be purified from the polymerase for example by phenolization. When the only analysis is by Southern blot, dot blot or in the MTP this is not necessary.

The newly formed nucleic acids are preferably separated as a double or as a single strand from the non-reacted mononucleoside triphosphates and primers by gel chromatography on affinity materials or by precipitation. In this connection, the process according to the present invention that uses a primer which is not modified with an immobilizable group is particularly advantagous since the separation of the newly formed nucleic acids from unmodified primers is particularly simple on solid phases which bind the immobilizable group.

The nucleic acids formed can, if desired, be separated from the template nucleic acid, for example by denaturing the double strand or via a replacement reaction. The newly formed nucleic acids can participate in further reactions, for example fragmentation by restriction enzymes such as in EP-A-0300796. They can also themselves be used as a template nucleic acid for the formation of nucleic acids in the processes according to the invention described above; these nucleic acids are then in turn at least partially complementary to them and homologous to the original template nucleic acid. A primer which is capable of hybridizing with the newly formed nucleic acid must then be used as primer instead of a nucleotide sequence complementary to the template nucleic acid. In other respects it must fulfill the conditions described above. Since also the original template nucleic acid is again available as a template for the formation of a new nucleic acid, this results in an at least approximately exponential multiplication of both the newly formed nucleic acid strands when each of the nucleic acids is used in a manner according to the present invention. This can occur in individual temperature or/and reagent cycles or even homogeneously. The reaction can in principle be stopped at any time by the addition of stop reagents (for example EDTA). In addition it is possible to modify the process according to the present invention such that so-called "nested" primers are used after some time in analogy to EP-A-0201184. From this time on only a part of the nucleic acid sequence produced up to then is amplified.

The processes can also be carried out such that the amount of nucleoside triphosphate enabling the immobilization which is available for the incorporation is limiting in the last reaction cycles. This has the advantage that the non-incorporated bio-nucleotides are consumed to a large extent in the reaction and thus do not compete any more with the bio-labelled amplification products for the SA binding sites. Therefore, a previous separation of the non-incorporated nucleotides (column or precipitation) is no longer necessary.

Nucleic acids or fragments thereof can also be used as template nucleic acids for the process according to the present invention like those that form as a result of nucleic acid amplification reactions for example of EP-A-0130229, EP-A-0300796, WO 88/10315, EP-A-0201184, EP-A-0329822, EP-A-0272098 or EP-A-0303155. In these cases it is possible, even if the elongation reaction is only carried out once, to produce, in accordance with the process according to the present invention, a large amount of nucleic acids modified according to the present invention.

The process carried out according to EP-A-0201184 using two mononucleoside triphosphates which are labelled differently such as biotin-16-dUTP (immobilizable, Leary et al., Proc. Natl. Acad. Sci. USA 80, 4045–49 (1983)) and digoxigenin-11-dUTP (detectable) represents a particularly preferred embodiment of the process.

The following experimental conditions have proven to be particularly expedient for this:

Volume of the reaction: 50–100 μl; concentration of the labelled primer 200 nM–1 μM; total concentration of the dNTP types: 100–300 μM; taq DNA polymerase: 1–3 U or another thermostable polymerase; buffer: 30–100 mM KCl; 5–20 nM Tris, pH 8.2–8.7 at rt; 0.5–2 mM $MgCl_2$; stabilizers, if desired, such as gelatin or nuclease-free BSA; PCR cycles: 20–60, preferably 20–30; denaturation: before the start 2–10 minutes, 92°–95° C. (optional; in the case of highly complex DNA), during PCR 1–5 minutes, 92°–95° C.; primer hybridization 1–5 minutes, 35°–75° C., elongation: 1–10 minutes, 65°–75° C., preferably 3 minutes, separation of the non-incorporated dNTP's and primer molecules from the nucleic acids formed at the end of the PCR. Sephadex C 75 or C 100 (Pharmacia) or a streptavidin solid phase (for example according to DE-A-3817716). The modified dNTP's can already be added from the first cycle or even be first added in the last 3–5 cycles. The latter procedure is recommended when bio-dUTP is added in limiting amounts. The ratio of the amount of specific primer to one another for each single strand is preferably ca. 1:1. Ratio of dig-dUTP:bio-dUTP:dTTP is 3:3:1 to 1:1:3, preferably 1:1:2 to 1:1:1. The ratio of dig-dUTP (or bio-dUTP): dTTP (when using a modified primer) is 3:1 to 1:3, preferably 1:2.

The above-mentioned values are approximate values. An expert can recognise straight away if conditions which deviate from these are also useful in the individual case.

It was surprising that it was possible by means of the present invention to be able to produce nucleic acids which can be immobilized better than expected and have the advantage that they can be quantitatively detected in a simple manner.

These advantages can be applied particularly well to methods for the detection of nucleic acids. The invention thus also provides a method for the detection of nucleic acids by the formation of a strand which is complementary to at least a part of a strand of the nucleic acid to be detected, binding of the nucleic acid formed to a solid phase and detection of the nucleic acid formed, in which the complementary strand is formed by hybridization of at least one primer to a template nucleic acid and enzymatic elongation of the primer to a nucleic acid strand complementary to the template nucleic acid by reaction with different types, preferably at least four types, of mononucleotides using the nucleic acid to be detected as the template nucleic acid and wherein the complementary nucleic acid strand carries two or more groups which enable it to be immobilized and one or more detectable groups.

In this process the nucleic acid to be detected or a part thereof which is, if desired, pretreated or for example amplified as described above serves as the template nucleic acid of the production process according to the present invention.

The nucleic acid strands which form as a result of the process can subsequently be detected in a very simple manner. These double strands can, if desired, be converted into single strands. The twice modified nucleic acids which form can for example be detected by gel chromatography. They are, however, preferably brought into contact with a suitable solid phase and immobilized there.

The type of solid phase depends on the group which enables the immobilization. If the immobilizable group is for example a hapten, then a solid phase can be used which has antibodies against this hapten on its surface. If the immobilizable group is a vitamin such as e.g. biotin then the solid phase can contain immobilized binding protein such as avidin or streptavidin. Immobilization via a group on the modified nucleic acid is particularly advantageous since it can take place under milder conditions than for example hybridization reactions.

In order to immobilize the nucleic acids which form it is preferred that, after completion of the process for the production of nucleic acids, a vessel is filled with the reaction mixture which can react on its surface with the immobilizable group. The vessel can for example be a cuvette or a microtitre plate. It is, however, also possible to use a solid phase in the form of a porous material such as a membrane, a tissue or a pad onto which the reaction mixture is loaded. The use of so-called beads is also possible.

After an incubation period during which the immobilization reaction takes place, the liquid phase is removed from the vessel, the porous material or the pelleted beads. The solid phase can subsequently be washed with a suitable buffer since the binding of the nucleic acid according to the present invention to the solid phase is very tight.

The amount of modified nucleic acid bound to the solid phase can in principle be determined in a known way whereby the steps which have to be carried out depend on the type of the detectable group. In the case of directly detectable groups, such as for example fluorescent labels, the amount of label is determined fluorometrically. If the detectable group is a hapten then the modified nucleic acid is preferably reacted with a labelled antibody against the hapten as described analogously in EP-A-0324474. The label can for example be an enzyme label such as β-galactosidase, alkaline phosphatase or peroxidase. In the case of an enzyme label the amount of nucleic acid is usually measured by photometric, chemiluminometric or fluorometric monitoring of a reaction of the enzyme with a chromogenic, chemiluminogenic or fluorogenic substrate.

In the case of indirectly detectable groups the required reagents (for example a labelled antibody directed towards a hapten) can also already be added to the reaction mixture before the washing step.

The detection of the nucleic acid can be carried out qualitatively as well as quantitatively. In the case of a quantitative evaluation it has turned out to be expedient to carry out at least one comparative test with a sample of known nucleic acid content. The establishment of a calibration curve is also possible and is recommended.

The method of detection according to the present invention can be applied to all the areas mentioned in EP-A-0200362. The method can also be applied to virus and bacterial diagnostics according to EP-A-0229701 and EP-A-0131052.

A particularly preferred embodiment of the method of detection according to the present invention encompasses the particularly preferred embodiment of the production process and a subsequent detection of the newly formed nucleic acid. The following general conditions have proven to be particularly advantageous for the detection: separation of the nucleic acids which form on a streptavidin surface (DE-A-3817716) for 1 to 4 hours at 37° C.; wash with buffer; incubation with a solution of an antibody against digoxigenin which is labelled with alkaline phosphatase; wash with buffer; incubation with 4-methylumbelliferyl phosphate, 0.05 to 0.2M; measuring in a fluorometer; comparison with a calibration curve.

The invention also provides a single- or double-stranded nucleic acid which is characterized in that it has one or more detectable groups and 2 or more groups which enable it to be immobilized in a nucleic acid strand. These modified nucleic acids have for example the advantage that they are capable of being immobilized very tightly on suitable solid phases. They can be produced using a template nucleic acid in a manner in accordance with the present invention. They can, however, also be produced in another way, for example by transcription in analogy to DE-A-3726934 if corresponding mononucleoside triphosphates (immobilizable and detectable groups) are used. Often no primers are needed for this.

The invention also provides reagent kits for carrying out the method according to the present invention for the detection of nucleic acids. One of these reagent kits contains in separate containers a first mononucleoside triphospate which carries a detectable group a second mononucleoside triphosphate which carries a group which enables the immobilization and an enzyme which by use of a template nucleic acid and four mononucleotides can form a nucleic acid which is complementary to the template nucleic acid.

In addition, it preferably contains all other reagents which are required for the elongation of primers to nucleic acids which are complementary to a nucleic acid strand. This includes, in particular, one primer which is specific for the nucleic acid or nucleic acid species to be detected as well as all other mononucleoside triphosphates. In addition, it can contain as auxilary substances suitable pH buffer substances, denaturing solutions and washing solutions.

It preferably also contains a specific nucleotide sequence which can hybridize with the primer as a control.

If desired, the reagent kit also contains the reagents which are necessary for the determination of the detectable group. If a hapten is used, then a labelled antibody is for example included in a separate container.

Another reagent kit contains in separate containers:
at least one primer which is essentially complementary to the nucleic acid to be detected and which carries two or more groups which enable the immobilization,
at least one mononucleoside triphosphate which carries a detectable group and
an enzyme which can, by use of a template nucleic acid of a primer and four mononucleotides, form a nucleic acid complementary to the template nucleic acid.

It also preferably contains all other reagents which are required for the elongation of primers.

In this case these include, in particular, the other mononucleoside triphosphates. Also the said auxilary agents, control nucleic acids and reagents for the detection of the group are preferably contained therein.

EXAMPLE 1

Figure 1:
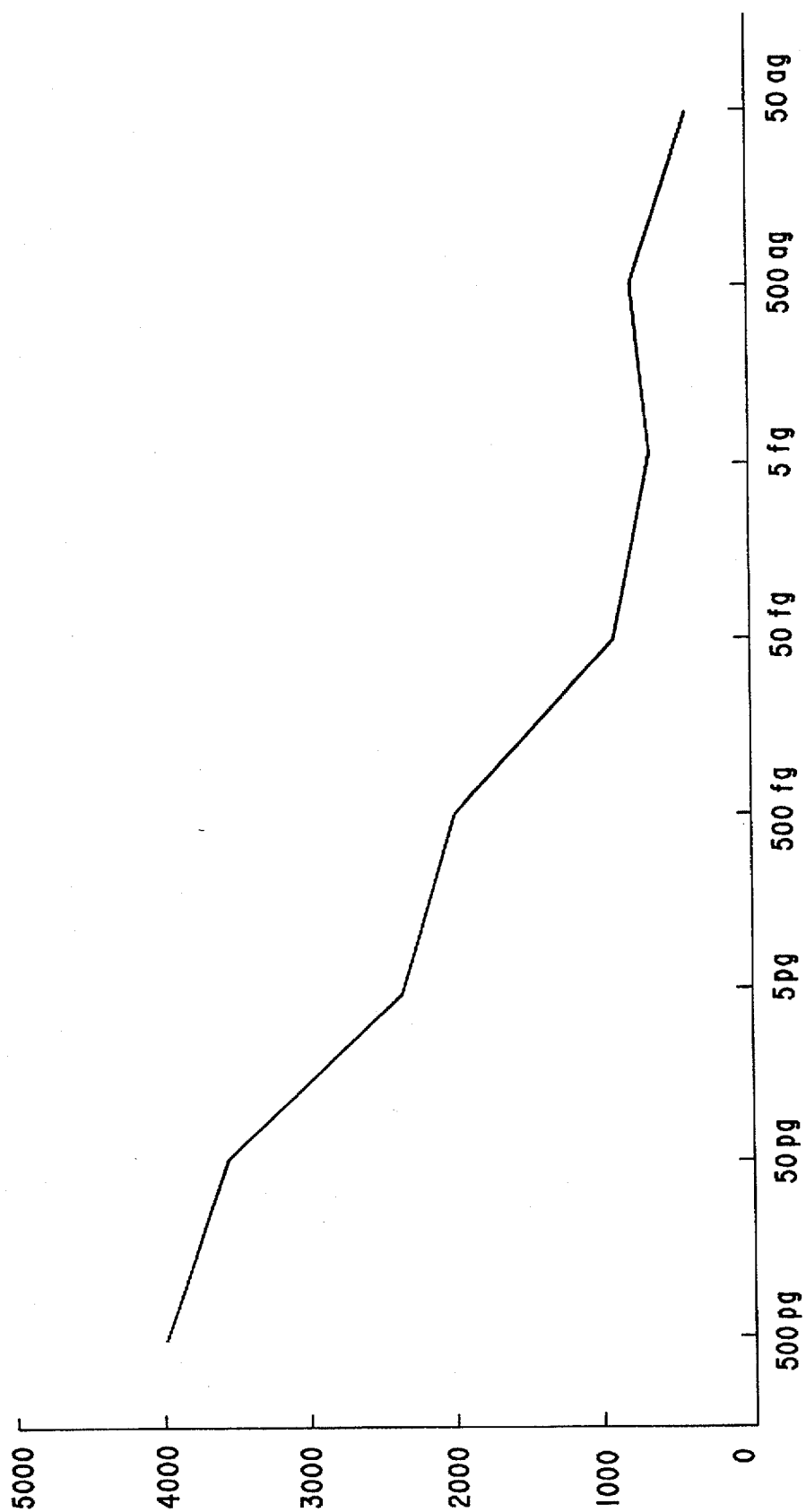
FIG. 1 shows the result of a determination of nucleic acids according to the method in accordance with the present invention. These results can also be used as a calibration curve.

Polymerase chain reaction (PCR) with two different modified mononucleotide triphosphates Dilutions of 10 ng–100 ag of the plasmid pSPT18neo (template nucleic acid, produced according to Beck et al., in Gene 19:327–336 (1982)) are used for the PC reaction according to EP-A-0200362. pSPT18neo contains the sequence of the neomycin(neo) gene in a 940 bp SmaI-BglII fragment in the SmaI-BamHI site of pSPT 18. The specifically amplified fragment corresponds therefore to 2.3 ng–23 ag in the plasmid dilutions. The reaction is started with specific primers (Boehringer Mannheim, Order no. 1175122 and 902152) for the T7 and SP6 promoters which flank the neo sequence in this plasmid. 30 PCR cycles are carried out in a volume of 50 µl in KCl, 50 mM; Tris HCl, pH 8.5, 10 mM; $MgCl_2$, 1.5 mM; gelatin, 100 µg/ml; dATP, 200 µM; dCTP, 200 µM; dGTP, 200 µM; dTTP, 100 µM; digoxigenin-11-2'-deoxyuridine-5'-dUTP (dig-11-dUTP, EP-A-0324474), 50 µm; biotin-16-2'-deoxyuridine-5'-triphosphate (bio-16-dUTP, Boehringer Mannheim GmbH, Order no. 1093070), 50 µM; with primer specific for the T7 promoter, 300 nM; and primer specific for the SP6 promoter, 300 nM; using the said pSPT18neo dilutions and 2.5 U *Thermus aquaticus* (Taq)-DNA polymerase.

Cycles
  denaturation: 2 minutes at 92° C.
  primer hybridization: 2 minutes at 42° C.
  elongation: 2 minutes at 75° C.

The PCR is carried out in a thermal cycler (DNA Thermal Cycler Perkin Elmer Cetus). The reaction volumes are covered with 30 µl paraffin in order to protect them from evaporation.

After the PC reaction, 5 µl 4M LiCl are added to the PCR products and they are precipitated in 250 µl ethanol for 30 minutes at –70° C. pelleted at 15000 g for 5 minutes, washed twice with 70% ethanol, dried, taken up in 50 µl Tris, pH 7.5, 10 mM and pipetted into a microtitre plate coated with streptavidin. Binding of the biotin/digoxigenin-labelled molecules to the streptavidin solid phase is carried out at 37° C. for 2 hours. After binding to the solid phase it is washed 3 times for 10 minutes with 2× SSC at 37° C. and once for 10 minutes with conjugate buffer (Tris HCl, pH 7.5, 100 mM; NaCl 0.9%; BSA, 1%; Pluronic T68, 0.5%) at 37° C. Afterwards it is incubated with 40 U anti-digoxigenin-alkaline phosphatase conjugate for 30 minutes at 37° C. and subsequently washed 5 times each with 200 µl of Tris-HCl, 100 mM; and NaCl, 150 mM. Finally it is incubated for 30 minutes at 37° C. with 4-methylumbelliferyl phosphate (0.1 mM) and measured in a Dynatech Microfluor Reader.

FIG. 1 shows the detection of ⅕ of the amplification preparation in each case in a streptavidin tube. The fluorescent signal is plotted against the concentration of template nucleic acid. Signals between 100 and 500 fg can be easily measured.

EXAMPLE 2

PCR with primers which have been modified several times

The PCR is carried out as in Example 1 with the same target and in the same concentrations. In the PC reaction 30 cycles are carried out in KCl, 50 mM; Tris-HCl, pH 8.5, 10 mM; $MgCl_2$, 1.5 mM; gelatin 100 µg/ml; dATP, 200 µM, dCTP, 200 µM; dGTP, 200 µM; dTTP, 133 µM; Dig-11-dUTP, 66 µM; with primers specific for the T7 promoter, which is 5'-(amidocaproyl)-biotin labelled with N-(3-(N',N'-diisopropylaminomethoxyphosphinyloxy)-hexyl)-2,2,2-trifluoreacetamide (Aminolink 2 of Applied Biosystems, USA) according to EP-A-0 261 283, 300 nM; and a primer specific for the SP6 promoter, which is 5'-(amidocaproyl)-biotin-labelled via Aminolink 2, 300 nM; with the dilutions of pSPT18neo as mentioned in Example 1 and 2.5 U taq DNA polymerase with the same cycle profiles. After PCR the reaction volume is made up to 300 µl with 10 mM Tris, pH 8.5, centrifuged in a Sephadex G75 column at 2000 rpm for 5 minutes and the eluate is precipitated with 30 µl 4M LiCl in 750 µl ethanol for 30 minutes at –70° C. and also centrifuged and resuspended just as in Example 1. The detection reaction with anti-digoxigenin-alkaline phosphatase conjugate is carried out as in Example 1.

EXAMPLE 3

Binding of nucleic acids labelled several-fold with biotin to streptavidin

Sandwich hybridization experiments are carried out with recombinant hepatitis B virus (HBV) DNA as template (0, 1, 5, 10, 20, 40, and 80 ng), a HBV-specific digoxigenin-labelled oligonucleotide (40 nucleotides, digoxigenin labelling with a digoxigenin molecule during the sythesis) as the detection probe and either a HBV-specific oligonucleotide (40 nucleotides) labelled once with biotin or an oligonucleotide of the same sequence labelled several times with biotin (8 biotin molecules/oligonucleotide) as the capture probe. Before the hybridization, the template DNA is denatured for 10 minutes at 100° C. and then immediately transferred onto ice. 200 ng each of the capture or the detection oligonucleotides are hybridized with the said amounts of recombinant HBV DNA in sodium phosphate, pH 6.8, 50 mM; 2× SSC (NaCl, 300 mM; $Na_3$ citrate, 30 mM); 5× Denhardt's solution (0.1% polyvinylpyrrolidone; 0.1% bovine serum albumin; 0.1% Ficoll 400) in a total volume of 200 µl in a streptavidin-coated tube for 60 min at 37° C.

Afterwards it is washed for 2×10 min at 37° C. with 200 µl SSC, 2×/SDS, 0.2% and 1× with 0.9% NaOH for 10 min at 37° C. Subsequently it is incubated with 200 µl anti-digoxigenin-horseradish peroxidase conjugate (150 U/ml) at 37° C. in Tris-HCl, pH 7.5, 100 mM; NaCl 0.9%; BSA, 1%; Pluronic T68 0.5% and washed 5× with 0.9% NaCl. Subsequently it is incubated with 0.1% 2,2-azino-di-[3-ethylbenzthiazoline sulfonate (6)] (ABTS, BM No. 756407) in 200 µl ABTS buffer (BM No. 1112597) and the absorbance is measured at 405 nm.

It can be seen in Table 1 that the measurable absorbance (i.e. the number of streptavidin-bound sandwich molecules present) is higher when multiply-labelled capture probes are used (the other conditions being completely identical) This is an indication for an efficient binding of the molecules labelled several times with biotin.

TABLE 1

| HBV template ng | Absorbance oligo-capture probe 1 biotin molecule | Absorbance oligo-capture probe 8 biotin molecules |
|---|---|---|
| 0 | 121 | 113 |
| 1 | 126 | 135 |
| 5 | 135 | 148 |
| 10 | 146 | 180 |
| 20 | 179 | 232 |
| 40 | 231 | 332 |
| 80 | 319 | 672 |

We claim:

1. A process for the production of labelled nucleic acids comprising the steps of
   a) hybridizing at least one primer to a template nucleic acid, and
   b) enzymatically elongating the primer by reaction with a set of nucleoside triphosphates to produce a newly formed complementary nucleic acid strand having at least two immobilizable biospecific labels and at least one detectable biospecific label, wherein said set of nucleoside triphosphates comprises at least one type of nucleoside triphosphate with a detectable, biospecific label, the same or at least one other type of nucleoside triphosphate with an immobilizable, biospecific label and unmodified nucleoside triphosphates, and wherein said immobilizable biospecific label is different from said detectable biospecific label.

2. The process according to claim 1, wherein said primer contains at least one immobilizable, biospecific label.

3. The process according to claim 1, wherein newly formed complementary nucleic acids formed in step b) are incorporated into step a) to serve as a template nucleic acid.

4. The process according to claim 1, wherein said set of nucleoside triphosphates comprises detectably labelled nucleoside triphosphates, immobilizably labeled nucleoside triphosphates and unmodified nucleoside triphosphates in a mixture ranging from 1:1:1 to 1:1:2, wherein said unmodified nucleoside triphosphates include all 4 types of natural nucleoside triphosphates.

5. A process for the production of labelled nucleic acids comprising the steps of a) separating a nucleic acid into single strands which are used as template nucleic acids, b) hybridizing at least one primer to said template nucleic acids, c) enzymatically elongating said at least one hybridized primer in the presence of a set of different types of nucleoside triphosphates producing an elongation product having at least two immobilizable labels of the same type and at least one detectable label, wherein said elongation product is complementary to the template nucleic acid, and d) amplifying said elongation product by repeating steps a), b) and c) in the presence of said set of different types of modified nucleoside triphosphates wherein at least one type of said nucleoside triphosphates is bound to a detectable biospecific label and the same or at least one other type of nucleoside triphosphate is bound to an immobilizable biospecific label, wherein said immobilizable biospecific label is different from said detectable biospecific label.

6. The process according to claim 1, wherein said primer contains at least one detectable biospecific label.

7. The process according to claim 1, wherein the immobilizable, biospecific label of at least one type of nucleoside triphosphates is biotin.

8. The process according to claim 1, wherein the detectable biospecific label of at least one type of nucleoside triphosphates is digoxigenin.

9. The process according to claim 1, wherein said primer contains at least one detectable, biospecific label, and said set of nucleoside triphosphates contains at least one type of nucleoside triphosphate with biotin as an immobilizable, biospecific label and at least one type of nucleoside triphosphate with digoxigenin as a detectable biospecific label.

10. The process according to claim 1, wherein said primer contains at least one immobilizable label, and said set of nucleoside triphosphates contains at least one type of nucleoside triphosphate with biotin as an immobilizable, biospecific label, and at least one type of nucleoside triphosphate with digoxigenin as a detectable biospecific label.

11. The process according to claim 1, wherein said set of mononucleotides contains at least one type of mononucleotide in the unmodified form and the same type of mononucleotide with a detectable biospecific label or with an immobilizable, biospecific label.

12. The process according to claim 1, wherein said primer is unmodified at its 3'-end.

13. A process for the detection of a nucleic acid comprising the steps of:

a) hybridizing at least one primer to the nucleic acid, b) enzymatically elongating the primer by reaction with a set of nucleoside triphosphates to produce a newly formed complementary nucleic acid strand having at least two immobilizable biospecific labels and at least one detectable biospecific label wherein said set of nucleoside triphosphates comprises at least one type of nucleoside triphosphate with a detectable, biospecific label, the same or at least one other type of nucleoside triphosphate with an immobilizable biospecific label and unmodified nucleoside triphosphates, c) immobilizing the newly formed complementary nucleic acid by means of the at least two immobilizable biospecific labels, and d) detecting immobilization by means of the at least one detectable biospecific label.

* * * * *